(12) United States Patent
Ahn et al.

(10) Patent No.: US 6,615,640 B2
(45) Date of Patent: Sep. 9, 2003

(54) FINE FRICTION AND WEAR TEST APPARATUS FOR PLATE SPECIMEN

(75) Inventors: Hyo Sok Ahn, Seoul (KR); Choong Hyun Kim, Seoul (KR); Nikolai K. Myshkin, Gomel (BY); Oleg Y. Komkov, Gomel (BY); Andrei M. Dubravin, Gomel (BY)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/054,738

(22) Filed: Jan. 22, 2002

(65) Prior Publication Data

US 2003/0000282 A1 Jan. 2, 2003

(30) Foreign Application Priority Data

Jun. 30, 2001 (KR) .......................... 2001-38974

(51) Int. Cl.[7] ............. G01N 19/02; G01N 3/56
(52) U.S. Cl. ............................................... 73/9
(58) Field of Search ................... 73/7, 9, 10

(56) References Cited

U.S. PATENT DOCUMENTS

| | | | | |
|---|---|---|---|---|
| 2,005,521 A | * | 6/1935 | Harrington | 73/10 |
| 5,178,004 A | * | 1/1993 | Bandyopadhyay et al. | 73/147 |
| 6,167,745 B1 | * | 1/2001 | Hamer et al. | 73/9 |
| 6,457,345 B1 | * | 10/2002 | Gebert et al. | 73/7 |

* cited by examiner

Primary Examiner—Hezron Williams
Assistant Examiner—Charles D Garber
(74) Attorney, Agent, or Firm—Allen, Dyer, Doppelt, Milbrath & Gilchrist, P.A.

(57) ABSTRACT

A fine friction and wear test apparatus for a plate specimen comprises a fixing unit a driving unit installed on the fixing unit for fixing and moving a certain plate specimen, a ball specimen support member for rubbing and wearing the plate specimen, a rotation plate position controller fixed on the fixing unit for controlling the position of the ball specimen support member, a ball specimen controller for controlling the ball specimen support member, a controller for detecting the degree of a friction and wear of the plate specimen and controlling each mechanical and circuit part; and a power supply unit for supplying a power to a part which requires a certain power.

20 Claims, 12 Drawing Sheets

FINE FRICTION AND WEAR TEST APPARATUS FOR PLATE SPECIMEN

FIELD OF THE INVENTION

The present invention relates to a fine friction and wear test apparatus for a plate specimen, and in particular to a fine friction and wear test apparatus for a plate specimen which is capable of reciprocating a plate specimen support member which fixes a plate specimen, rubbing and wearing a plate specimen against a ball specimen attached to a ball specimen support member, measuring a degree of a friction and wear of the plate specimen using a laser source and accurately analyzing the characteristic of the plate specimen.

BACKGROUND OF THE INVENTION

Generally, a friction and wear test apparatus is an apparatus capable of rubbing and wearing a certain specimen using a certain tool and analyzing a friction and wear characteristic of the specimen and is generally used for analyzing a friction of a small size mechanical part and analyzing the characteristic of the wear.

A conventional friction and wear test apparatus is classified into a big size apparatus which operates for a large weight above about 10N and operates in a minimum stroke range above about 10 mm, and a small size apparatus which operates for below about 1 $\mu$N and operates in a stroke range below about 1 $\mu$m.

However, since the above large size friction and wear test apparatus operates in a range in which the range of weight applied to specimen is large and the sliding speed is high, it is impossible to accurately analyze the friction and wear characteristic of a friction part of a fine machine which operates in a very lower weight range and a low speed range. In the fine friction and wear test apparatus, since a friction force measuring unit for measuring the degree of the friction of the specimen is engaged to a specimen table, if the specimen is moved, the friction force detector of the friction force measuring unit is moved, and the characteristic of the friction force detector is varied, so that it is impossible to accurately measure the characteristic of the friction and wear of the specimen.

SUMMARY OF THE INVENTION

Accordingly, it is an object of the present invention to provide a fine friction and wear test apparatus for a plate specimen capable of analyzing a friction and wear characteristic of a small size specimen for processing a small size parts which has a small friction and wear and is not stuck.

It is another object of the present invention to provide a fine friction and wear test apparatus for a plate specimen capable of analyzing a friction and wear characteristic of a specimen in a weight range of 1 $\mu$N~1N for processing a small size part which has a small friction and wear and is not stuck.

It is still another object of the present invention to provide a fine friction and wear test apparatus for a plate specimen capable of reciprocating a plate specimen support member in which a plate specimen is attached to a ball specimen of a ball plate specimen support member, rubbing and wearing the plate specimen, measuring the degree of a friction and wear of the plate specimen using a detector and accurately analyzing a friction and wear characteristic of the plate specimen.

It is further still another object of the present invention to provide a fine friction and wear test apparatus for a plate specimen which is capable of reciprocating a plate specimen support member to which a plate specimen is attached using a voice coil, rubbing and wearing the plate specimen against a ball specimen of a ball specimen support member, measuring the degree of a friction and wear of the plate specimen using a laser source and a light detector and accurately analyzing the characteristic of a friction and wear of the plate specimen.

To achieve the above objects, there is provided a fine friction and wear test apparatus for a plate specimen according to the present invention which includes a fixing unit which a pair of first fixing columns and a pair of second fixing columns are engaged on a bottom plate having a certain area in a vertical direction, a driving unit in which a stainless pipe is fixed to one side of the fixing unit, and the plate specimen support member of the other end horizontally reciprocates based on the operation of a first voice coil motor engaged to one end of the stainless pipe, a rotation plate position controller in which a rotation plate is vertically engaged to the lower end of the coil motor engaged to one side of each second fixing column, a ball specimen support member in which a ball specimen is engaged to one end of the load plate horizontally engaged to the rotation plate, and a balance weight is engaged to the other end of the same, a ball specimen engaged to an upper end of the second fixing column and controlling the movement of the ball specimen support member engaged to one end of the same, a control measuring unit installed in an upper end of the fixing unit for outputting a light to a reflection mirror and measuring a friction force of the plate specimen, and a power unit installed in one surface of the base for supplying a power to the driving unit, the rotation plate position controller and the control measuring unit.

To achieve the above objects, there is provided a fine friction and wear test apparatus for a plate specimen according to the present invention which includes a fixing unit which a pair of first fixing columns and a pair of second fixing columns are engaged on a bottom plate having a certain area in a vertical direction, a driving unit in which a stainless pipe is fixed to one side o the fixing unit, and the plate specimen support member of the other end horizontally reciprocates based on the operation of a first voice coil motor engaged to one end of the stainless pipe, a rotation plate position controller in which a rotation plate is vertically engaged to the lower end of the coil motor engaged to one side of each second fixing column, a ball specimen support member in which a ball specimen is engaged to one end of the load plate horizontally engaged to the rotation plate, and a balance weight is engaged to the other end of the same, a ball specimen engaged to an upper end of the second fixing column and controlling the movement of the ball specimen support member engaged to one end of the same, a control measuring unit installed in an upper end of the fixing unit for outputting a light to a reflection mirror and measuring a friction force of the plate specimen, and a power unit installed in one surface of the base for supplying a power to the driving unit, the rotation plate position controller and the control measuring unit.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE PREFERRED EMBODIMENTS

The preferred embodiments of the present invention will be explained with reference to the accompanying drawings.

Figure 1:
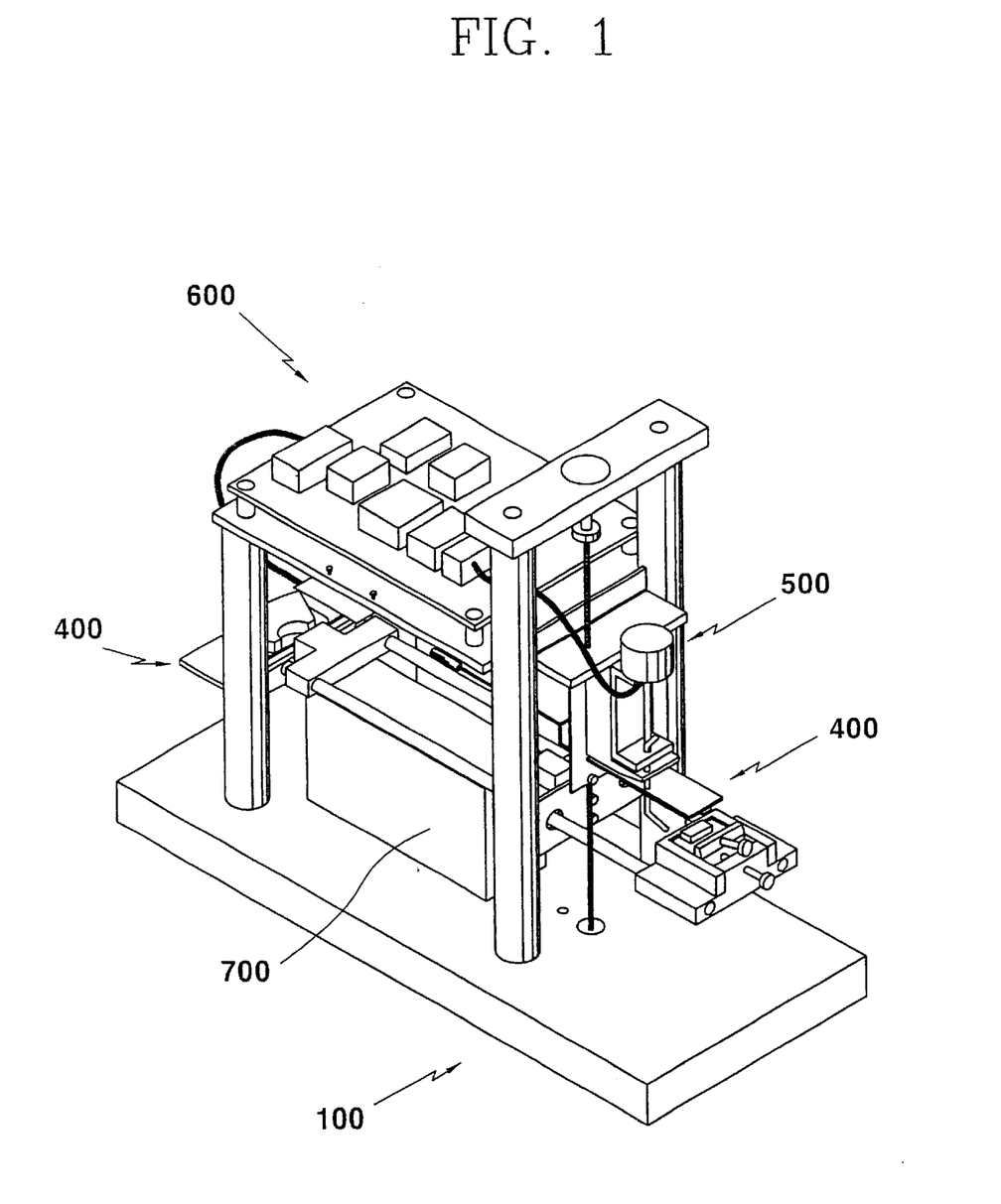
FIG. 1 is a perspective view illustrating a fine friction and wear test apparatus for a plate specimen for rubbing and wearing a plate specimen according to the present invention.
Figure 2A:
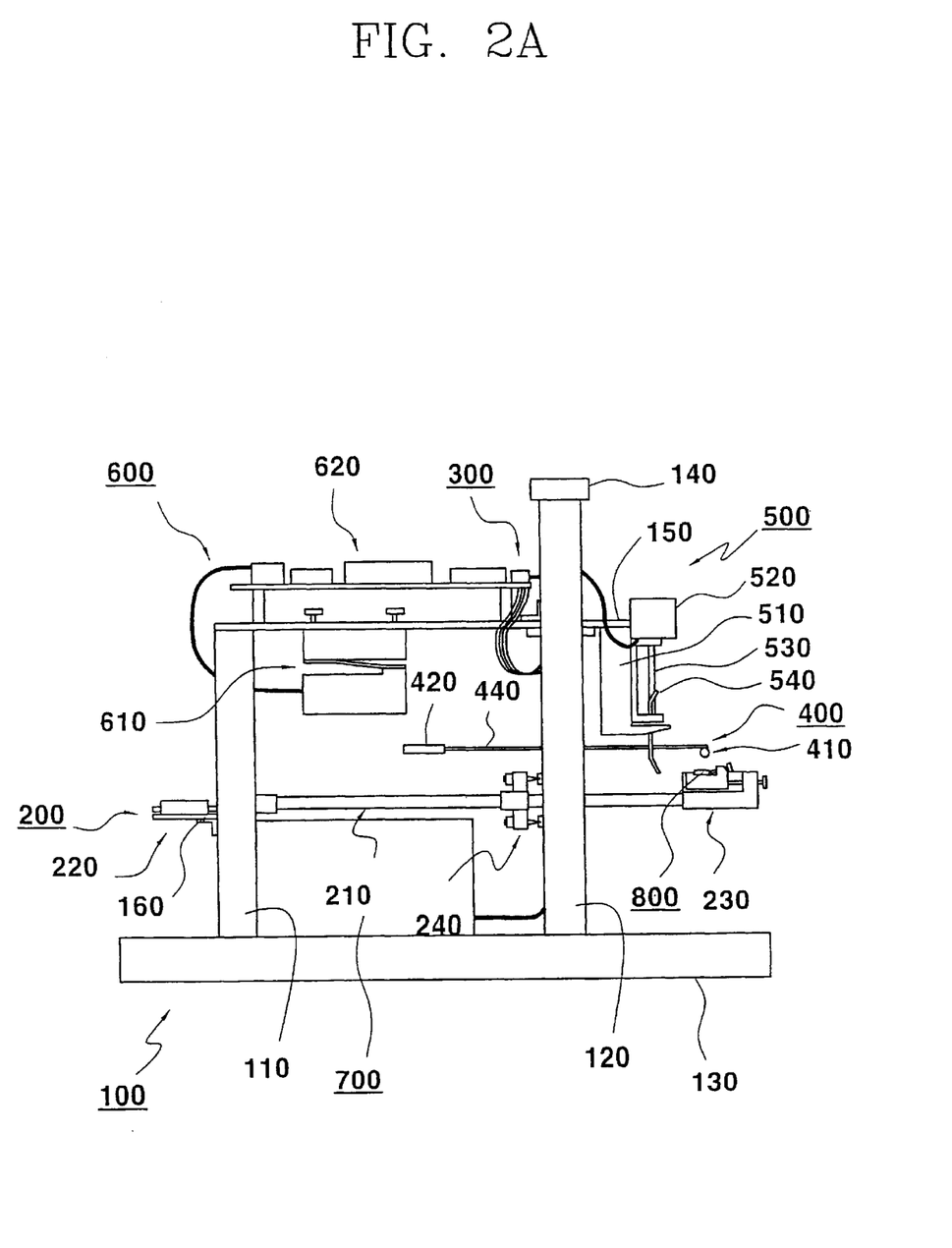
FIGS. 2A and 2B are side views of FIG. 1.
Figure 2B:
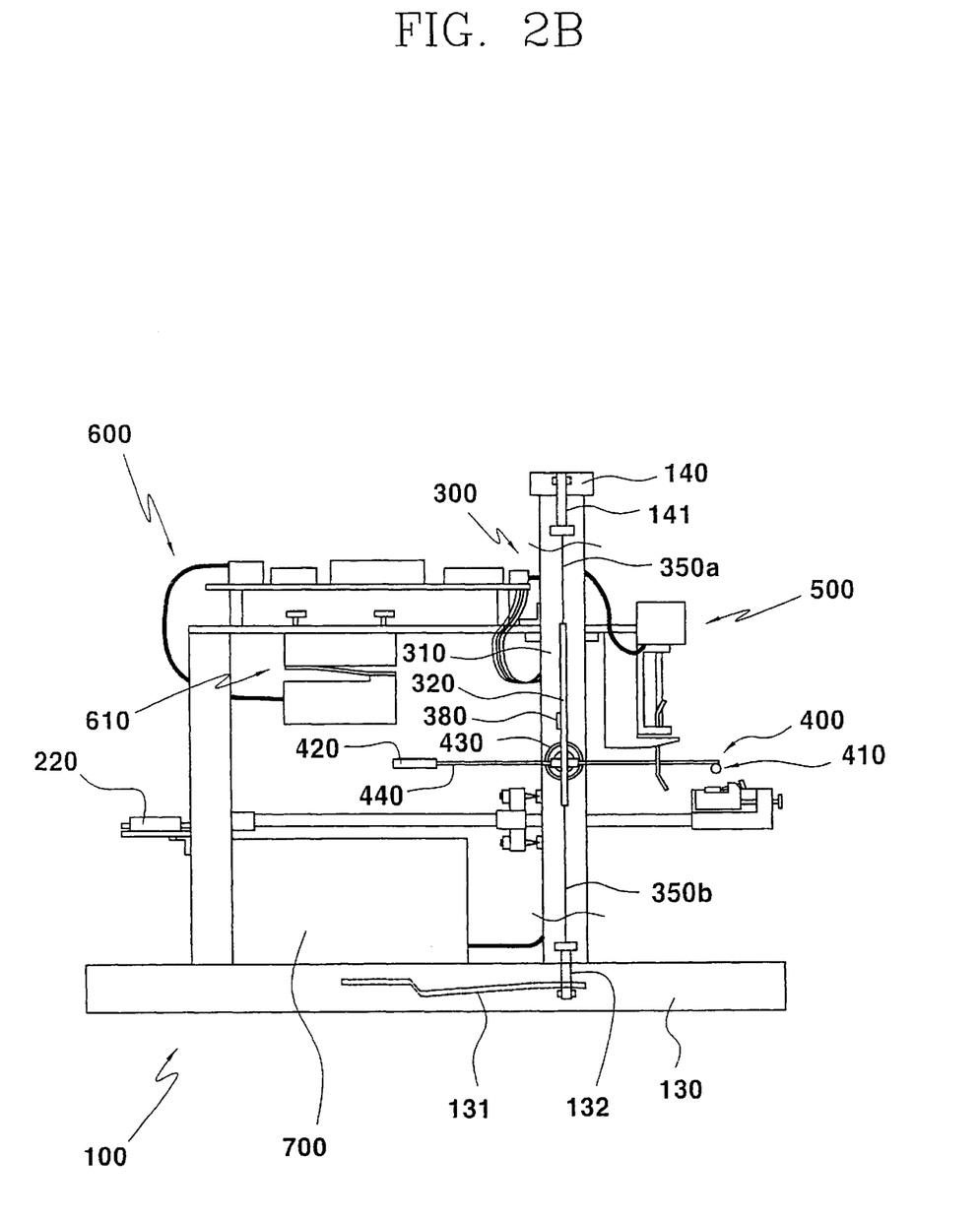

FIG. 1 is a perspective view illustrating a fine friction and wear test apparatus for a plate specimen for rubbing and wearing a plate specimen according to the present invention, and FIGS. 2A and 2B are side views of FIG. 1.

As shown therein, a fine friction and wear test apparatus for a plate specimen according to the present invention includes a fixing unit 100, a driving unit 200 installed on the fixing unit 100 for fixing and moving a plate specimen 800, a ball specimen support member 400 for rubbing and wearing the plate specimen 800, a rotation plate position controller 300 fixed on the fixing unit 100 for controlling the position of the ball specimen support member 400, a ball specimen controller 500 for controlling the ball specimen support member 400, a controller 600 for detecting the degree of a friction and wear of the plate specimen 800 and controlling each mechanical and circuit part, and a power supply unit 700 for supplying a power to a part which requires a certain power.

The fixing unit 100 includes a bottom plate 130 having a certain area, a pair of first fixing columns and a pair of second fixing columns installed at a certain position of each corner portion of the bottom plate 130, an upper end upper portion 140 for connecting the upper end of the second fixing column 120, an upper plate 150 for fixing the upper ends of the first fixing columns 110 and the positions of the second fixing columns 120 having the same height as the first fixing columns 110, a plate spring 131 installed in the interior of the bottom plate 130 and having a certain elastic coefficient, a first adjusting screw 132 connected with the plate spring 131 and protruded from the upper surface of the bottom plate 130, and a second adjusting screw 141 installed in the center portion of the upper end support portion 140 and corresponding to the first adjusting screw 132.

Figure 3:
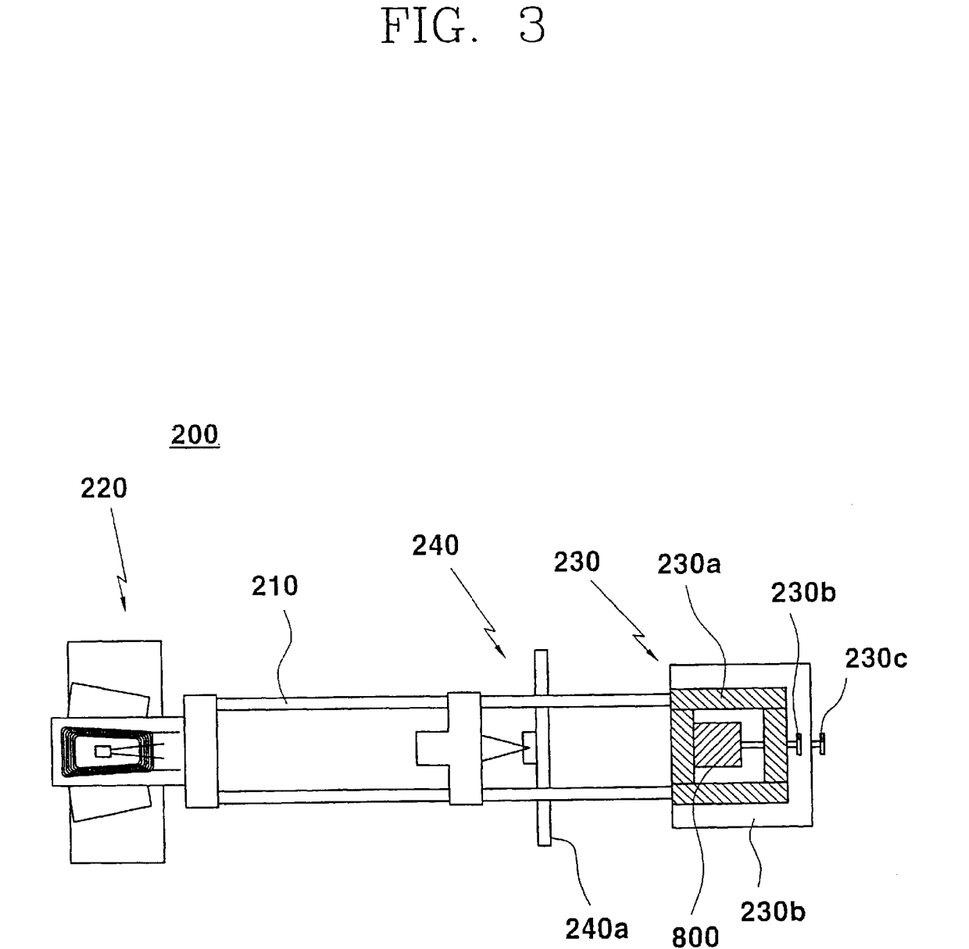
FIG. 3 is a plan view illustrating a driving unit of FIG. 1.

As shown in FIG. 3, the driving unit 200 installed between the bottom plate 130 and the upper plate 150 in parallel with the bottom plate 130 and the upper plate 150, respectively, includes a stainless pipe 210 installed between the first fixing columns 110 and the second fixing columns 120, a first voice coil motor 220 attached to the end of the stainless pipe 210, a fixing plate 240a, through which the stainless pipe 210 passes, installed in the second fixing column 120 and supporting the stainless pipe 210, a needle support member 240 for supporting the stainless pipe 210 to the fixing plate 240a, and a plate specimen support member 230 engaged to the other end of the stainless pipe 210 for fixing and supporting the plate specimen 800.

The plate specimen support member 230 includes a plate specimen holder 230a for receiving the plate specimen 800 therein, a first fixing screw 230b for fixing the plate specimen 800 to the plate specimen holder 230a, a plate specimen holder engaging portion 230d for receiving the plate specimen holder 230a therein, and a second fixing screw 230c for fixing the plate specimen holder 230a to the plate specimen holder portion 230d. The plate specimen holder engaging portion 230d fixes the plate specimen holder 230a and moves the plate specimen holder 230a as the second adjusting screw 230c is adjusted. Therefore, the plate specimen support member 230 adjusts the position contacting with the ball specimen 410 by adjusting the position of the plate specimen 800.

Figure 4A:
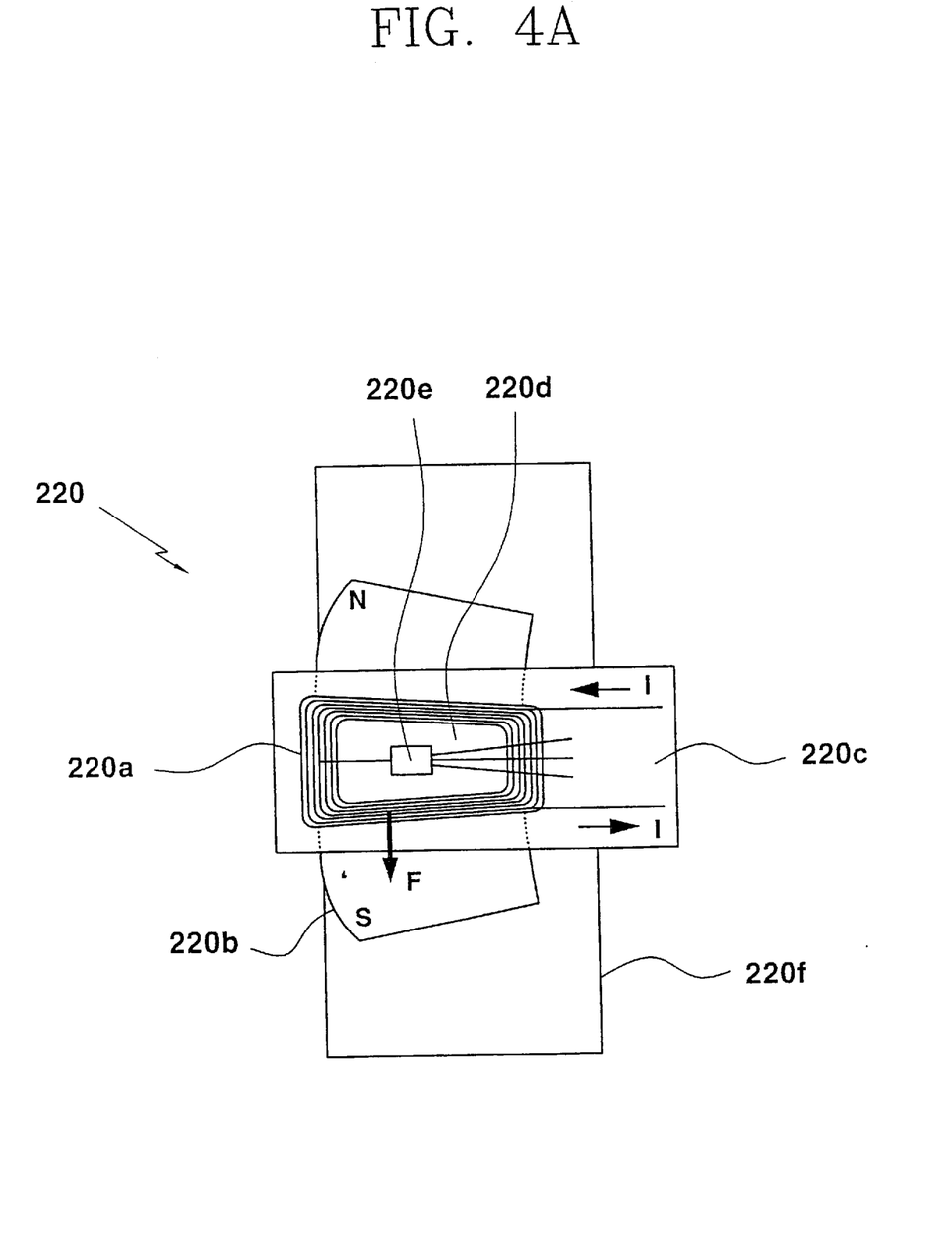
FIG. 4A is a view illustrating the construction of a first voice coil motor unit of FIG. 3.
Figure 4B:
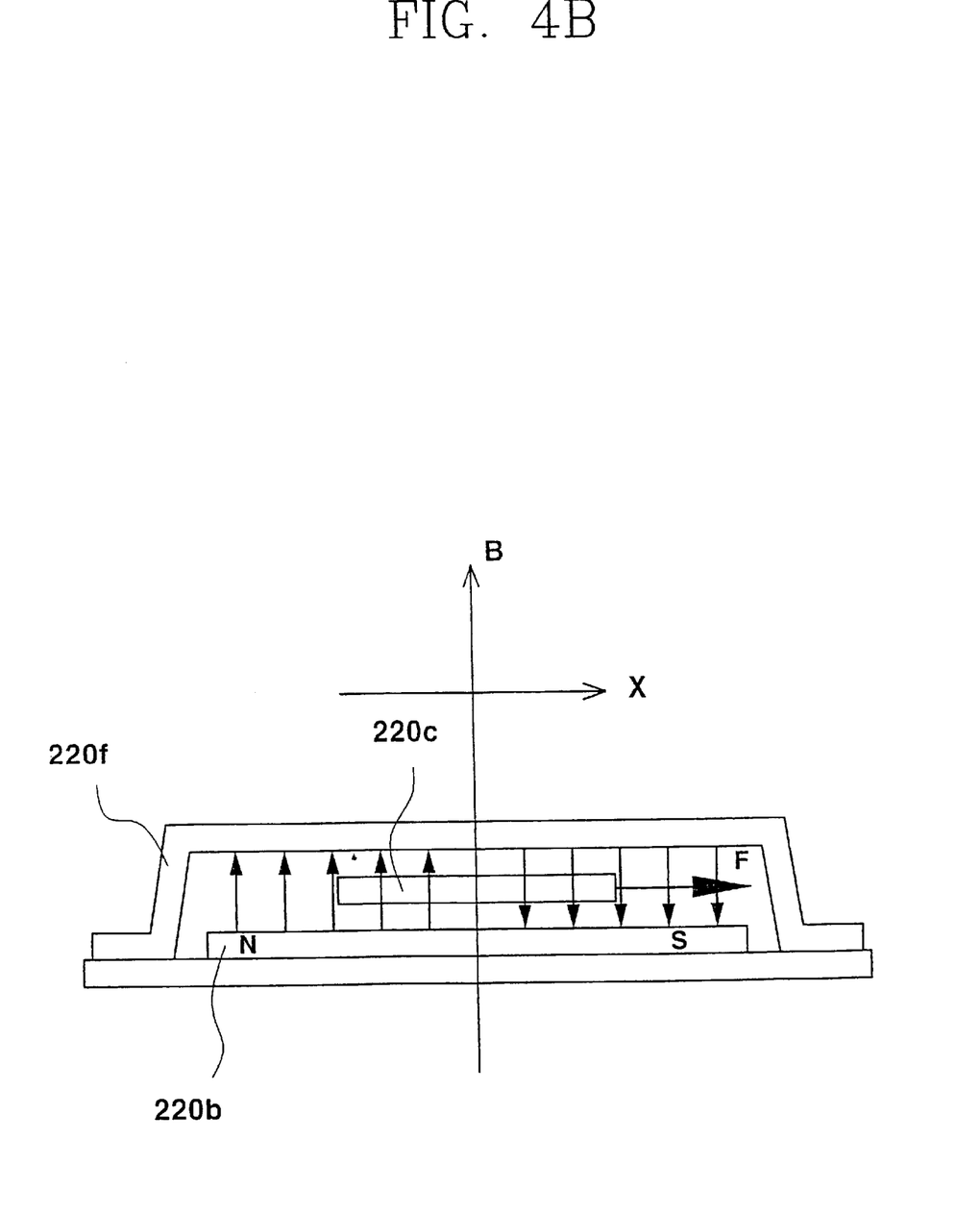
FIG. 4B is a side view of FIG. 4A.

As shown in FIGS. 4A and 4B, the first voice coil motor 220 includes an aluminum frame 220c connected with one end of the stainless pipe 210, an aluminum core 220d fixed to a groove formed in the inner side of the aluminum frame 220c using an adhesive, a wire 220a wound along the groove formed in the outer side of the aluminum core 220d, a magnetic field sensor 220e fixed to the inner side of the aluminum core 220d using an adhesive, a permanent magnet 220b installed in the lower portion of the aluminum frame 220c for generating a certain magnetic field, and a magnetic guide 220f for fixing the permanent magnet 220b and guiding a magnetic field.

Figure 4C:
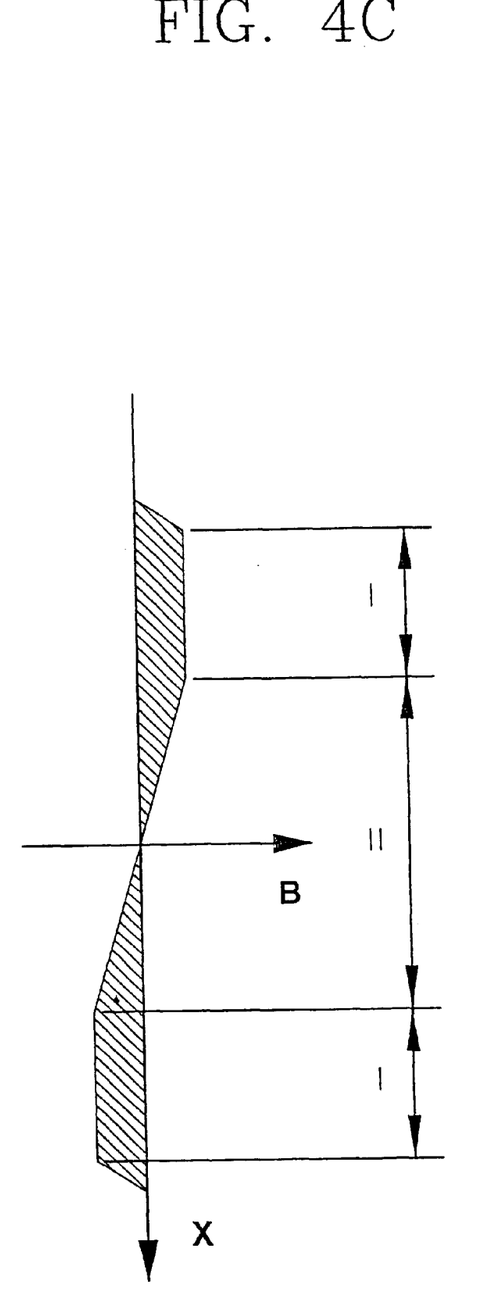
FIG. 4C is a view illustrating an operation of a first voice coil motor unit of FIGS. 4A and 4B.
Figure 4D:
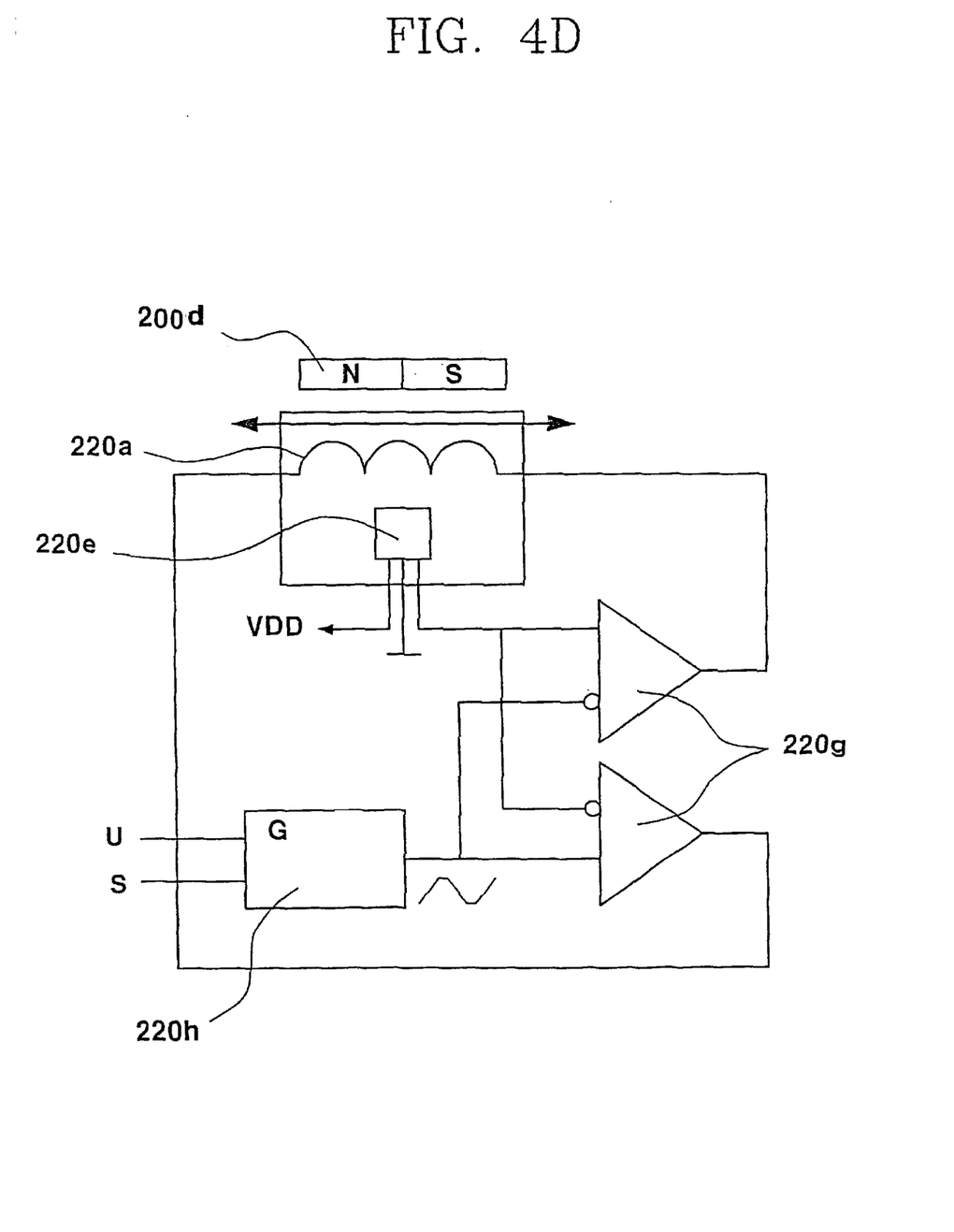
FIG. 4D is a circuit diagram for controlling a first voice coil motor unit of FIGS. 4A and 4B.

As shown in FIG. 4D, the circuit for operating the first voice coil motor 220 includes a digital signal generator 220h for receiving a reciprocating stroke S and moving speed U applied to the plate specimen 800 and outputting a certain pulse signal, and an amplifier 220g for receiving the pulse signal and a signal from the magnetic field sensor 220e and applying a corresponding current.

Figure 5:
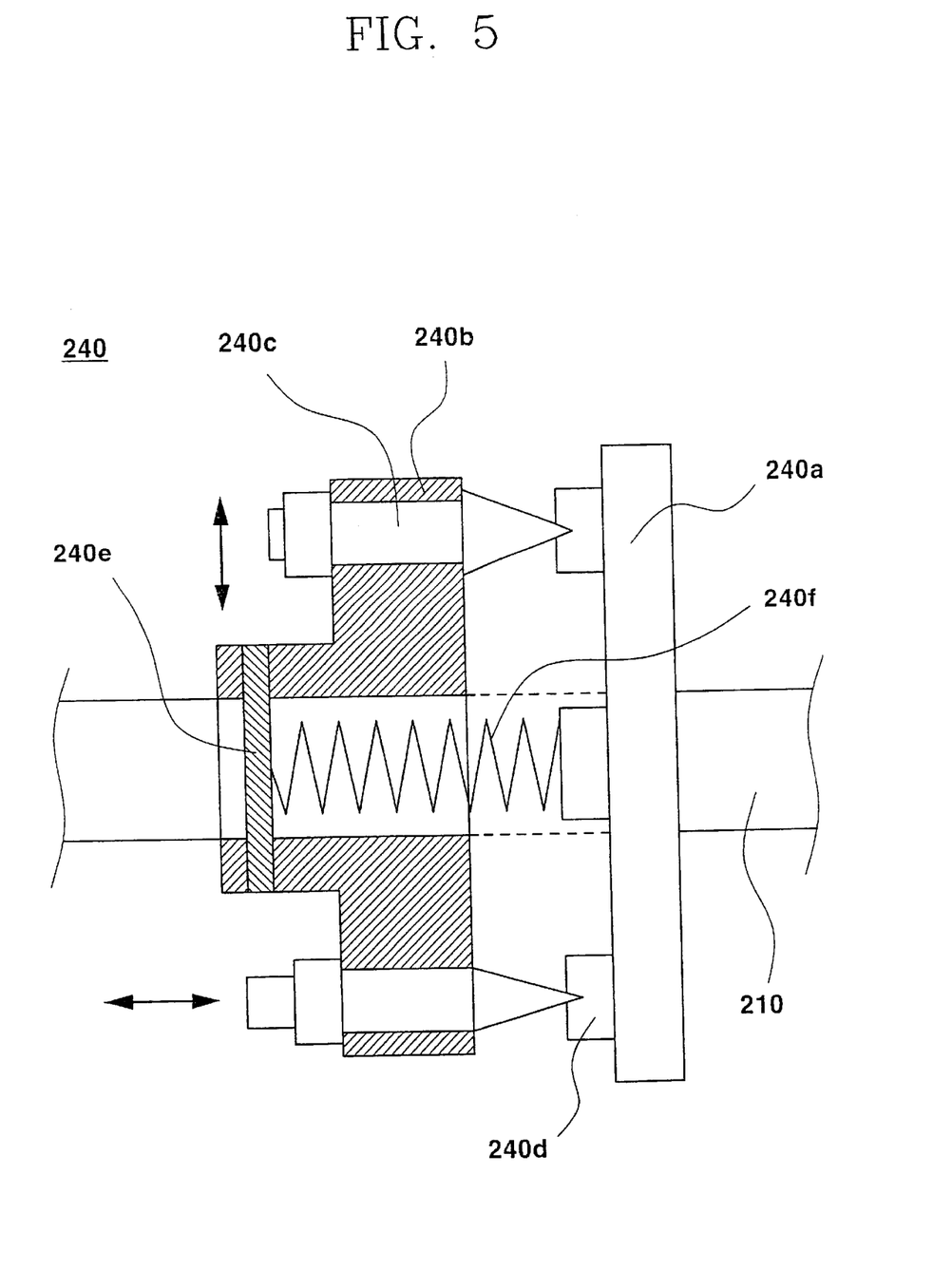
FIG. 5 is a view illustrating the construction of a needle support member of FIG. 3.

As shown in FIG. 5, the needle support member 240 includes a needle 240c for indicating a symmetric point from the center of the fixing plate 240a, an aluminum body 240b for fixing the needle 240c, a spring 240f for maintaining a certain distance between the fixing plate 240a and the aluminum body 240b and a support plate 240e installed in the aluminum body 240 for supporting the spring 240f. Here, the support member 240d contacting with the needle 240c is installed on the fixing plate 240a on the point of the needle 240c. The needle 240c is formed of a heat-treated steel and includes a conical groove formed in the center portion of the same and a body having a screw portion. Therefore, the position of the same is adjusted in the aluminum body 240b.

The needle support member 240 is fixed to the fixing plate 240a by a spring 240f that connects the spring support plate 240e and the fixing plate 240a, and a peak needle 240c is inserted into a conical groove of the support member 240d.

Figure 6A:
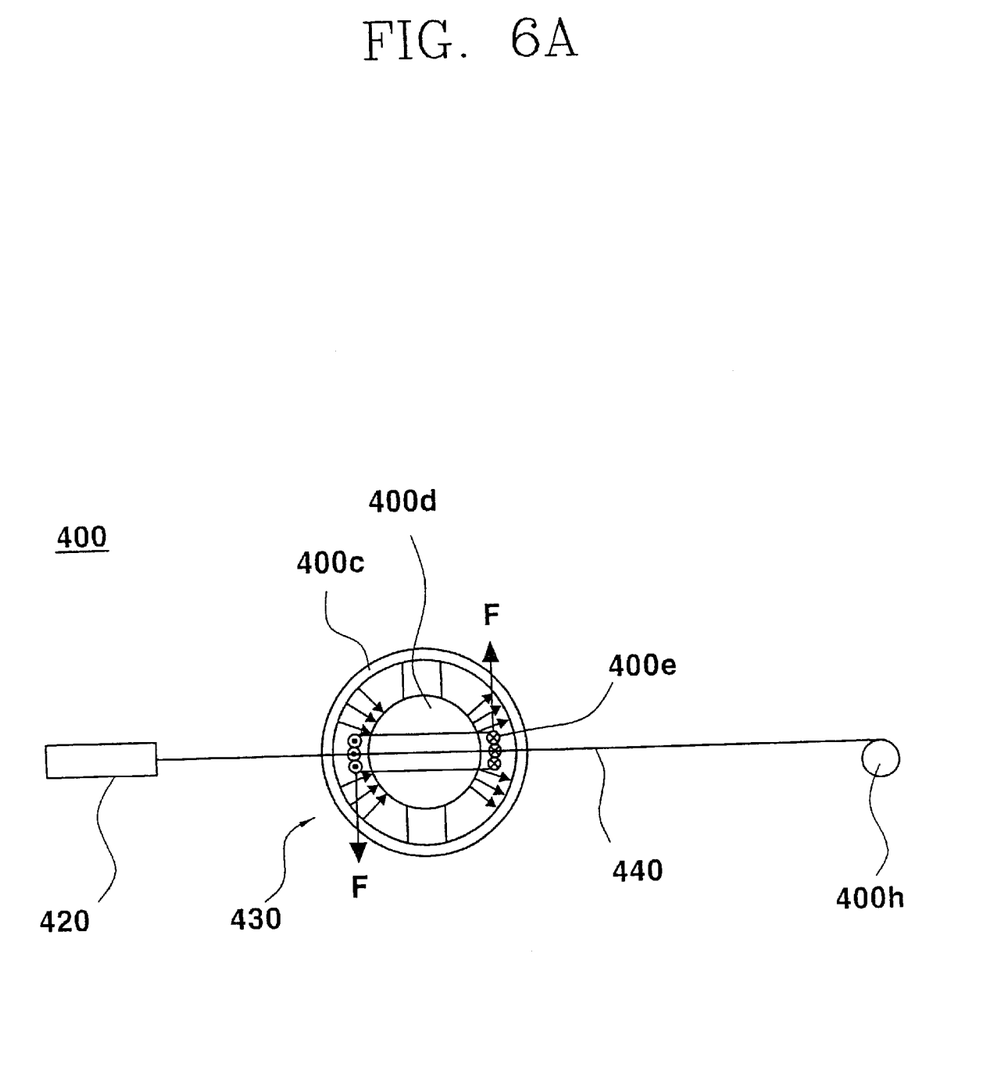
FIG. 6A is a side view illustrating a ball specimen support member of FIG. 1.
Figure 6B:
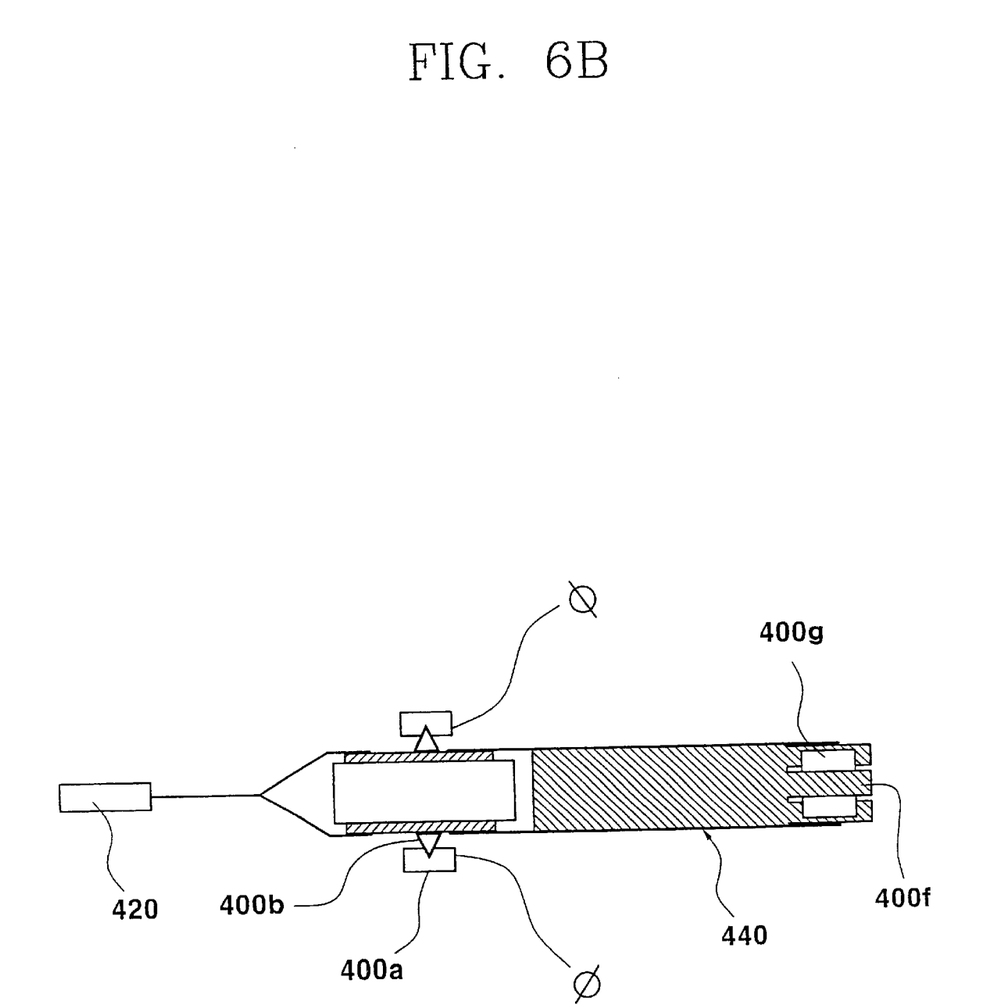
FIG. 6B is a plan view illustrating a ball specimen support member of FIG. 6A.

As shown in FIGS. 6A and 6B, the ball specimen support member 400 includes a ball specimen 410 for rubbing and wearing the plate specimen 800, a load plate 440 having one end attached with the ball specimen 410, a second voice coil motor 430 for operating the ball specimen 410 through the load plate 440, and a balance weight 420 attached to other side of the load plate 440 and being parallel with the ball specimen 410 with respect to the second voice coil motor 430.

The second voice coil motor 430 includes a circular permanent magnet 400d, a frame 400e installed near the permanent magnet 400d for winding a coil thereon, a steel ring 400c for surrounding the winding frame 400e, and a fixing needle 400b installed in an outer casing in such a manner that the balance weight 420 and the ball specimen 410 are parallel. The fixing needle 400b is supported by the fixing support member 400a installed in the casing in which surrounds the outer portions of the steel ring 400c.

The fixing needle 400b is formed of heat-treated steel, and the fixing support member 400a is formed of a copper.

The ball specimen 410 includes a ball specimen 400h for rubbing and wearing the plate specimen 800, a ball specimen holder 400g for fixing the ball specimen 400h and a ball specimen holder engaging portion 400f for fixing the ball specimen holder 400g.

The rotation plate position controller 300 includes a third voice coil motor 310, and a rotation plate 320 connected to a lower portion of the coil motor 310. Here, the upper portion of the rotation plate 320 is connected with the first adjusting screw 141 installed in the upper support portion 140 of the second fixing column 120 by a steel wire 350a. The lower portion of the rotation plate 320 is connected with the second adjusting screw 132 of the bottom plate 130 by a steel wire 350b. Since the second adjusting screw 132 is connected with a plate spring 131 installed in the interior of the bottom plate 130, a tension force of the plate spring 130 maintains a parallel state of the rotation plate 320 through the steel wire 350b.

A mirror 380 is attached to the rotation plate 320 for reflecting a light from the measuring unit 610 of the controller 600 which will be explained later.

The ball specimen controller 500 includes a housing 510 attached to a lower surface of one end of the upper plate 150, a stepping motor 520 installed in the corner portion between the fixing housing 510 and the upper plate 150, a screw shaft 530 for transferring a driving force generated by the stepping motor 520, and a guide 540 for converting the rotational movement of the screw shaft 530 and reciprocating the ball specimen support member 400.

The controller 600 includes a circuit 620 for controlling the entire elements of the apparatus, and a measuring unit 610 for outputting a light to the mirror 380 attached to the rotation plate 320, detecting a reflected light and measuring a friction force applied to the plate specimen 800.

Figure 7:
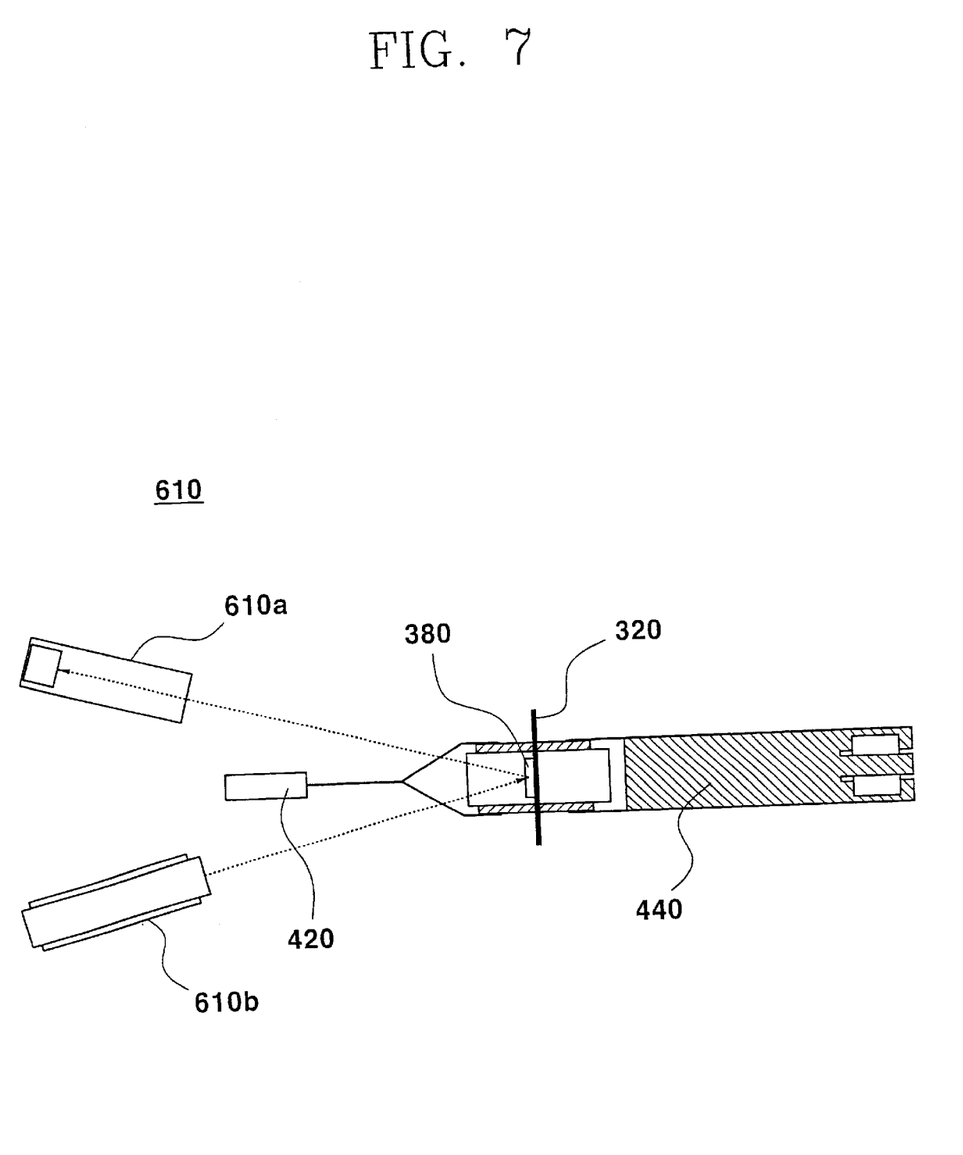
FIG. 7 is a view for explaining an operation of a measuring unit of FIG. 1.

As shown in FIG. 7, the measuring unit 610 includes a light source 610b for outputting a light to the mirror 380 of the rotation plate 320, and a light detector 610a for detecting a light reflected by the mirror 380.

The circuit 620 analyzes a signal from the light detector 610a, measures a rotational angle of the rotation plate 320 and a friction force of the plate specimen 430 and controls the rotation plate 320 to return to a reference position.

The operation of the fine friction and wear test apparatus for a plate specimen according to the present invention will be explained.

First, a plate specimen of an analysis object is fixed to the plate specimen support member. When a current is flown to the winding of the first voice coil motor, the frame having the winding in a magnetic field region formed by the permanent magnet is moved by a fore generated based on the Fleming's right hand law. Therefore, the driving unit to which the frame is attached reciprocates horizontally. Here, the needle support member becomes a center shaft of the horizontally reciprocating movement of the driving unit and operates as a hinge of the driving unit. The needle support member implements a rolling friction capable of moving the needle and support member without sliding. The driving unit has a small driving noise and decreases a mechanical friction heat of each part.

The force generated by the first voice coil motor enables the driving unit reciprocate. Since the friction force of the driving unit is small, and a movement transfer error of the driving unit is small, the reciprocating movement force of the driving unit is fully transferred to the plate specimen without a driving force loss. The minimum weight value of the driving unit is determined by a friction characteristic of the needle 240c and the needle support member 240. The weight resolving capacity of the fine test apparatus for a plate specimen is about 3 $\mu$N(0.3 mg).

The magnetic field sensor 220e detects a variation of the magnetic field intensity in a direction vertical to the magnetic field and outputs a signal proportional thereto. The magnetic field guide 220f transfers a magnetic field generated by the permanent magnet 220b to the aluminum frame and prevents the same from being spread to the outside and forms a closed magnetic field.

As shown in FIG. 4C, in the region II in which a variation of the magnetic field intensity is linear, the first voice coil motor controller receives a magnetic force variation signal from the magnetic field sensor 220e and checks the position of the frame 220c and controls the motion of the same for thereby adjusting the reciprocating movement of the plate specimen support member 230 connected with the frame 220c. The frame 220c having the winding 220a reciprocates in the region to which the maximum driving force is applied. The displacement control resolving capacity of the stroke of the reciprocating movement is about 0.05 $\mu$m.

As the plate specimen support member is moved, when a friction force is generated between the plate specimen and the ball specimen 410, the friction force is transferred to the rotation plate 320 through the ball specimen support member 400, so that the rotation plate is rotated, and the rotation plate position controller 300 controls the movement of the rotation plate 320.

When a current is flown from the power supply unit to the coil wound in the winding frame 400e of the second voice coil motor, a force F is generated based on an inter-operation with the magnetic field formed by the circular permanent magnet 400d. The force F is transferred to the load plate 440 and outputs a weight between the ball specimen 410 and the plate specimen 430.

At this time, the circular permanent magnet 400d forms a certain size magnetic field in the direction vertical to the winding in all radius directions surrounded by the steel ring 400c. Therefore, in the case of the same current, the operation weight is constantly formed irrespective of the circular direction position of the winding frame 400e.

The load plate 440 is connected with an outer portion of the winding frame 400e, and the ball specimen holder engaging portion 400f is formed in one side, and the balance weight 420 is engaged to the other side. The ball specimen holder 400g is formed of a thin metallic plate. The ball specimen 410 is inserted into or is boned with the ball specimen holder 400g. The ball specimen holder 400g having the inserted and bonded the ball specimen 410 is inserted into the ball specimen holder engaging portion 400f.

The ball specimen 410 is easily changed, and it is possible to decrease the weight and the accuracy of the test apparatus is enhanced. The heat-treated fixing needle 400b and the copper fixing support member 400a do not have any friction loss and small error due to the movement. Therefore, it is proper to transfer the lower weight using the circular permanent magnet 400d and the winding frame 400e.

The current is supplied to the coil wound on the winding frame 400e through the fixing support member 400a. The horizontal state of the load plate 400 is maintained before the operational weight is applied by controlling the current supplied to the winding of the winding frame 400e. Therefore, even when the weight of the ball specimen 410 is varied, it is possible to accurately adjust the operational weight.

The step motor 520 of the ball specimen controller 500 generates a rotational movement through the screw shaft 530, and the rotational movement is converted into a linear movement through the guide 540. The guide 540 controls the movement of the ball specimen support member 400 which receives the weight. The ball specimen 410 and the plate specimen 430 are guided for thereby being contacted by a proper contact force, and the ball specimen support member 400 is protected from an external factor.

The rotation plate position controller 300 connected with the circuit 620 detects the size of the rotational angle of the rotation plate when the plate specimen 800 is rubbed and worn out and measures the friction force based on the value of the rotational angle and enables the rotation plate 320 return to a reference position. Namely, when a light is outputted from the light source to the mirror of the rotation plate, the light detector detect a light reflected from the mirror of the rotation plate and detects the position of the rotation plate.

The rotation plate position controller 300 controls the size and direction of the current value supplied from the power supply unit to itself and measures the friction force generated in the plate specimen 430 and positions the rotation plate 320 in the reference position. Since the size and direction of the current inputted into the rotation plate position controller are proportional to the friction force between the ball specimen and the plate specimen, it is possible to obtain an information concerning the friction force of the plate specimen from the values corresponding to the size and direction of the current.

Therefore, the fine test apparatus for a plate specimen according to the present invention rubs and wears the plate specimen 430 contacting with the ball specimen and measures and analyzes in real time the friction and wear of the plate specimen for thereby controlling the control software installed in the computer. The computer obtains a test information of the plate specimen and sets the movement speed of the plate specimen and a weight value of the ball specimen applied to the reciprocating stroke and plate specimen and controls the test apparatus.

As described above, in the fine test apparatus for rubbing and wearing the plate specimen according to the present invention, the plate specimen support member reciprocates by the first voice coil motor and rubs and wears the plate specimen and measures the characteristic of the plate specimen.

In the fine test apparatus for rubbing and wearing the plate specimen according to the present invention, the weight range is about 50 $\mu$N~0.01N, and the maximum reciprocating stroke is 2 mm, and the maximum reciprocating speed is 1.3 mm/s, and the weight and the resolving capacity of the reciprocating stroke are below 5 $\mu$N, and 0.05 $\mu$m, respectively, for thereby implementing a high accuracy control.

In addition, in the present invention, the size of the operational weight and the reciprocating period are continuously controlled for analyzing the friction and wear of the plate specimen and the driving unit is capable of rubbing and wearing the specimen in real time.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A fine friction and wear test apparatus for a plate specimen, comprising:
    a fixing unit comprising
        a bottom plate having a certain area,
        a pair of first fixing columns and a pair of second fixing columns installed in a position of each corner potion of the bottom plate,
        an upper end support portion for connecting the upper end of the second fixing columns,
        an upper plate for fixing an upper end of the first fixing column and the position of the second fixing column having the same height as the first fixing column,
        a plate spring installed in the interior of the bottom plate and having a certain elastic coefficient,
        a first adjusting screw connected with the plate spring and protruded on the upper surface of the bottom plate, and
        a second adjusting screw installed in the center portion of the upper end support portion and corresponding to the first adjusting screw,
    a driving unit installed on the fixing unit for fixing and moving a certain plate specimen;
    a ball specimen support member for rubbing and wearing the plate specimen;
    a rotation plate position controller fixed on the fixing unit for controlling the position of the ball specimen support member;
    a ball specimen controller for controlling the ball specimen support member;
    a controller for detecting the degree of a friction and wear of the plate specimen and controlling each mechanical and circuit part; and
    a power supply unit for supplying a power to a part which requires a certain power.

2. The apparatus of claim 1, wherein said driving unit includes:
    a stainless pipe installed between the first fixing columns and the second fixing columns;
    a first voice coil motor attached to the end of the stainless pipe;
    a fixing plate for supporting the stainless pipe, the fixing plate is installed in the second fixing column and is penetrated through the stainless pipe;
    a needle support member for supporting the fixing plate; and
    a plate specimen for fixing and supporting the plate specimen, the plate specimen is installed at the other end of the stainless pipe.

3. The apparatus of claim 2, wherein said plate specimen support member includes:
    a plate specimen holder for receiving the plate specimen therein;
    a first fixing screw for fixing the plate specimen to the plate specimen holder;

a plate specimen holder engaging portion for receiving the plate specimen holder therein; and a second fixing screw for fixing the plate specimen holder to the plate specimen holder portion.

4. The apparatus of claim 3, wherein said first voice coil motor includes:

an aluminum frame connected with one end of the stainless pipe;

an aluminum core fixed to a groove formed in the inner side of the aluminum frame using an adhesive;

a wire wound along the groove formed in the outer side of the aluminum core;

a magnetic field sensor fixed to the inner side of the aluminum core using an adhesive;

a permanent magnet installed in the lower portion of the aluminum frame for generating a certain magnetic field; and a magnetic guide for fixing the permanent magnet and guiding a magnetic field.

5. The apparatus of claim 4, wherein said needle support member includes:

a needle for indicating a symmetric point from the center of the fixing plate;

an aluminum body for fixing the needle;

a spring for maintaining a certain distance between the fixing plate and the aluminum body; and a support plate installed in the aluminum body for supporting the spring.

6. The apparatus of claim 1, wherein said ball specimen support member includes:

a ball specimen for rubbing and wearing the plate specimen;

a load plate having one end attached with the ball specimen;

a second voice coil motor for operating the ball specimen through the load plate;

and a balance weight attached to other side of the load plate and being parallel with the ball specimen with respect to the second voice coil motor.

7. The apparatus of claim 6, wherein said second voice coil motor includes:

a circular permanent magnet;

a frame installed near the circular permanent magnet for winding a coil thereon;

a steel ring for surrounding the winding frame; and a fixing needle installed in an outer casing in such a manner that the balance weight and the ball specimen are parallel.

8. The apparatus of claim 6, wherein said ball specimen includes:

a ball specimen for rubbing and wearing the plate specimen;

a ball specimen holder for fixing the ball specimen therein; and a ball specimen holder engaging portion for fixing the ball specimen holder.

9. The apparatus of claim 2, wherein said rotation plate position controller includes:

a third voice coil motor; and a rotation plate connected to a lower portion of the coil motor.

10. The apparatus of claim 1, herein said ball specimen controller includes:

a housing attached to a lower surface of one end of the upper plate;

a stepping motor installed in the corner portion between the fixing housing and the upper plate;

a screw shaft for transferring a driving force generated by the stepping motor; and a guide for converting the rotational movement of the screw shaft and reciprocating the ball specimen support member.

11. The apparatus of claim 1, wherein said controller includes:

a circuit unit for controlling the entire elements of the apparatus; and a measuring unit for outputting a light to the mirror attached to the rotation plate, detecting a reflected light and measuring a friction force applied to the plate specimen.

12. A fine friction and wear test apparatus for a plate specimen, comprising:

a fixing unit which a pair of first fixing columns and a pair of second fixing columns are engaged on a bottom plate having a certain area in a vertical direction;

a driving unit in which a stainless pipe is fixed to one side of the fixing unit, and the plate specimen support member of the other end horizontally reciprocates based on the operation of a first voice coil motor engaged to one end of the stainless pipe;

a rotation plate position controller in which a rotation plate is vertically engaged to the lower end of the coil motor engaged to one side of each second fixing column;

a ball specimen support member in which a ball specimen is engaged to one end of the load plate horizontally engaged to the rotation plate, and a balance weight is engaged to the other end of the same;

a ball specimen engaged to an upper end of the second fixing column and controlling the movement of the ball specimen support member engaged to one end of the same;

a control measuring unit installed in an upper end of the fixing unit for outputting a light to a reflection mirror and measuring a friction force of the plate specimen; and a power unit installed in one surface of the base for supplying a power to the driving unit, the rotation plate position controller and the control measuring unit.

13. The apparatus of claim 12, wherein said driving unit includes:

a stainless pipe which is engaged with one side of each of the first fixing columns and the second fixing columns in a horizontal direction and has a certain length;

a first voice coil motor engaged with one end of the stainless pipe for generating a certain force based on an inter-operation between the current applied to the winding and the permanent magnet;

a needle support member which passes through the stainless pipe and fixes the fixing plate; and a plate specimen support member engaged to the other end of the stainless pipe for enabling the plate specimen be rubbed and worn by the ball specimen.

14. The apparatus of claim 13, wherein said plate specimen support member has a contact point with the ball specimen which is adjusted by adjusting the plate specimen fixing screw and the plate specimen holder adjusting screw after inserting the plate specimen into the plate specimen holder.

15. The apparatus of claim 12, wherein said rotation plate position controller connects a steel wire to the fixing unit and upper end support portion for thereby implementing a certain tension force.

16. The apparatus of claim 15, wherein one end of the steel wire is connected with a plate spring installed in the interior of the fixing unit, and the other end of the same is connected with an adjusting screw engaged to the upper end support portion.

17. The apparatus of claim 12, wherein said control measuring unit includes:

- a light detector for outputting a light to a reflection mirror attached to one side of the rotation plate vertically engaged to a lower portion of the coil motor and measuring a reflected light; and
- a circuit for measuring a friction force of the plate specimen based on a rotation angle of the rotation plate and enabling the rotation plate be returned to a reference position.

18. The apparatus of claim 12, wherein said ball specimen controller includes:

- a housing fixed to an upper end of the second fixing column;
- a stepping motor engaged to one end of the fixing housing;
- a screw shaft vertically engaged to a lower end of the step motor and being horizontally rotated; and
- a guide with one end of the screw shaft and converting a horizontal rotation movement into a linear reciprocating movement and guiding the movement of the ball specimen support member.

19. The apparatus of claim 12, wherein in said ball specimen support member, a ball specimen which rubs and wears the plate specimen is engaged with one end of the load plate, and a balance weight is engaged to the other end of the load plate for thereby maintaining a balance of the specimen.

20. The apparatus of claim 12, wherein said ball specimen controller is elastically connected with a circuit of the control measuring unit for thereby controlling movement of the ball specimen support member.

* * * * *